(12) United States Patent
Cowan

(10) Patent No.: US 9,408,981 B2
(45) Date of Patent: Aug. 9, 2016

(54) ADJUSTABLE VOLUME SYRINGE

(71) Applicant: MEDRAD, INC., Indianola, PA (US)

(72) Inventor: Kevin P. Cowan, Allison Park, PA (US)

(73) Assignee: Bayer HealthCare LLC, Whippany, NJ (US)

(*) Notice: Subject to any disclaimer, the term of this patent is extended or adjusted under 35 U.S.C. 154(b) by 557 days.

(21) Appl. No.: 13/792,158

(22) Filed: Mar. 10, 2013

(65) Prior Publication Data

US 2014/0257233 A1     Sep. 11, 2014

(51) Int. Cl.
*A61M 31/00*      (2006.01)
*A61M 5/315*      (2006.01)
*A61M 5/178*      (2006.01)
*A61M 5/20*       (2006.01)

(52) U.S. Cl.
CPC ....... *A61M 5/31563* (2013.01); *A61M 5/31596* (2013.01); *A61M 5/1785* (2013.01); *A61M 5/20* (2013.01); *A61M 5/31561* (2013.01); *A61M 2005/1787* (2013.01); *A61M 2005/31598* (2013.01); *A61M 2205/50* (2013.01); *A61M 2205/505* (2013.01); *A61M 2205/52* (2013.01)

(58) Field of Classification Search
CPC ...................... A61M 5/31565; A61M 5/31596; A61M 2005/31598; A61M 5/1785; A61M 2205/52; A61M 5/31561; A61M 2005/1781; A61M 2205/50
See application file for complete search history.

(56) References Cited

U.S. PATENT DOCUMENTS

| | | |
|---|---|---|
| 984,037 A | 2/1911 | Sheets |
| 2,869,543 A | 1/1959 | Ratcliff et al. |
| 4,188,949 A | 2/1980 | Antoshkiw |
| 5,032,117 A * | 7/1991 | Motta ............... A61M 5/14 604/187 |
| 5,300,041 A | 4/1994 | Haber et al. |
| 5,512,054 A | 4/1996 | Morningstar |
| 5,522,804 A | 6/1996 | Lynn |

(Continued)

FOREIGN PATENT DOCUMENTS

EP        2222358        9/2010
WO    2012006555 A1    12/2012

OTHER PUBLICATIONS

International Search Report for Counterpart PCT Application No. PCT/US2014/022383.

(Continued)

*Primary Examiner* — Nathan R Price
*Assistant Examiner* — Morgan Lee
(74) *Attorney, Agent, or Firm* — Joseph L. Kent; David Schramm; James R. Stevenson

(57) ABSTRACT

Adjustable volume syringes and systems are disclosed. An adjustable volume syringe includes a delivery syringe barrel, a reservoir syringe barrel positioned at least partially within the delivery syringe barrel, and a reservoir plunger positioned at least partially within the reservoir syringe barrel. The delivery syringe barrel is configured to contain a first amount of a fluid. The reservoir syringe barrel is configured to contain a second amount of the fluid. A system includes the adjustable volume syringe, a dispensing module in communication with the syringe, and a processor in communication with the dispensing module. The processor may be configured to determine an administration amount of the fluid in the adjustable volume syringe, and transmit signals causing the dispensing module to adjust the volume of fluid in the syringe to the administration amount and deliver the administration amount by moving the reservoir syringe barrel with respect to the delivery syringe barrel.

14 Claims, 7 Drawing Sheets

(56) References Cited

U.S. PATENT DOCUMENTS

| | | |
|---|---|---|
| 5,665,068 A | 9/1997 | Takamura |
| 5,769,824 A | 6/1998 | Hjertman et al. |
| 5,971,953 A | 10/1999 | Bachynsky |
| 7,632,245 B1 | 12/2009 | Cowan et al. |
| 8,021,343 B2 | 9/2011 | Nalesso et al. |
| 8,075,533 B2* | 12/2011 | Lee .................. A61M 5/31596 604/191 |
| 8,529,517 B2 | 9/2013 | Lee |
| 2005/0277833 A1* | 12/2005 | Williams .......... A61M 5/16827 600/431 |
| 2006/0084909 A1 | 4/2006 | Tai |
| 2008/0287913 A1 | 11/2008 | Schwab |
| 2009/0247985 A1 | 10/2009 | Melsheimer et al. |
| 2010/0228121 A1 | 9/2010 | Kazuhiro et al. |
| 2010/0286513 A1 | 11/2010 | Pollard, Jr. et al. |
| 2012/0130236 A1 | 5/2012 | Nystrom |

OTHER PUBLICATIONS

International Search Report and Written Opinion dated Sep. 9, 2014 re PCT/US14/24265.

The International Preliminary Report on Patentability and Written Opinion mailed on Sep. 24, 2015 from corresponding PCT Application No. PCT/US2014/022383.

* cited by examiner

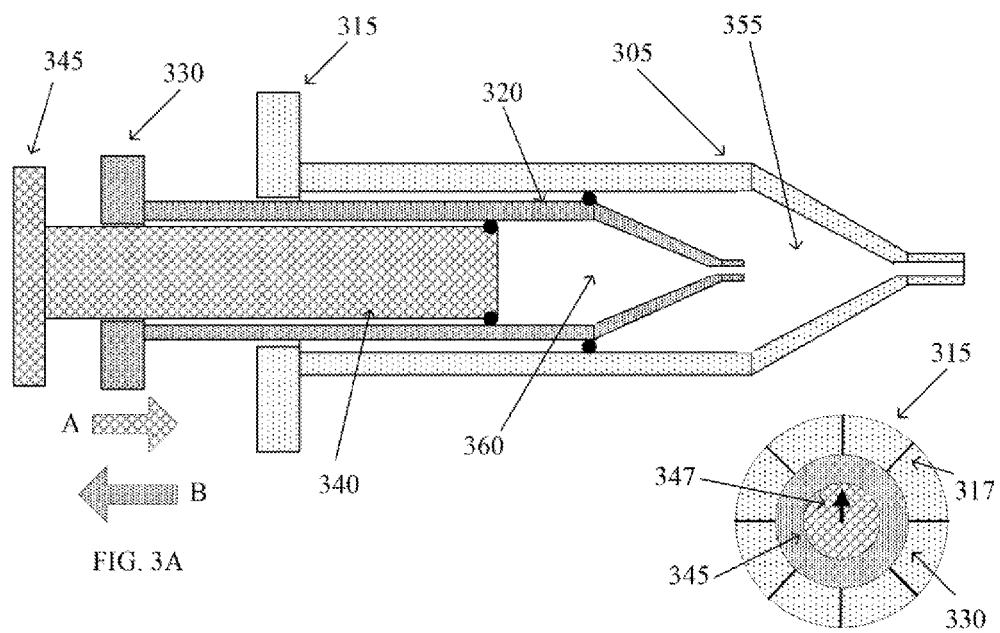
FIG. 3A
FIG. 3C
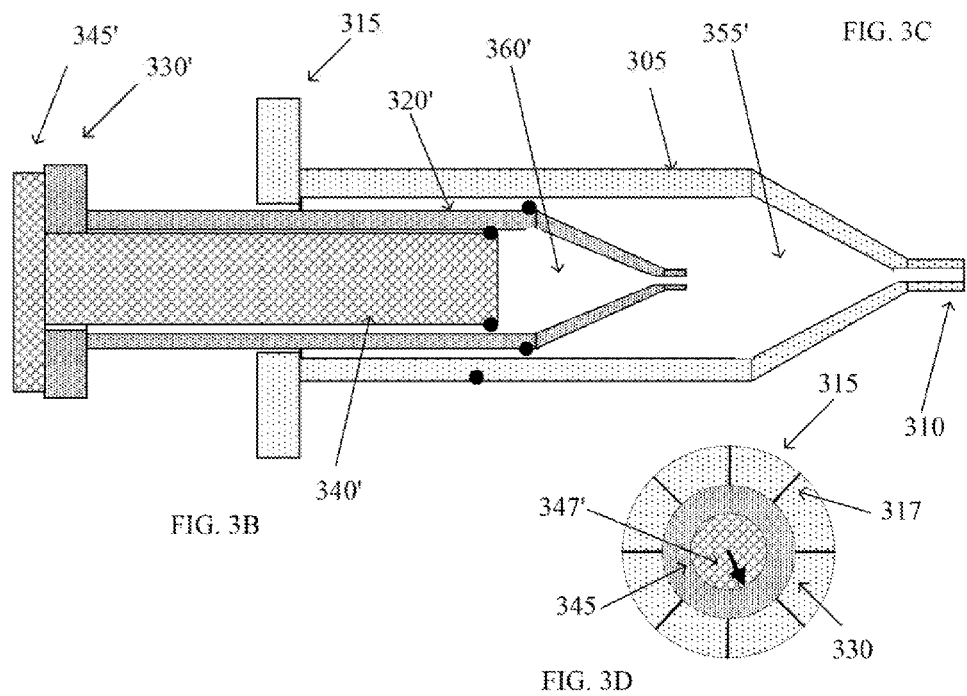
FIG. 3B
FIG. 3D

ADJUSTABLE VOLUME SYRINGE

BACKGROUND

Positron emission tomography (PET) and single photon emission computed tomography (SPECT) procedures typically rely on positron or gamma ray emitting radionuclides with short half-lives. For example, PET procedures frequently rely on $^{18}$F-deoxyglucose (FDG) while many SPECT procedures rely on conjugated $^{99m}$Tc compounds.

$^{18}$F has a half-life of less than 2 hours, while $^{99m}$Tc has a half-life of about 6 hours. The volume of a solution carrying a tracer must be carefully calculated for administration of a specific radiation dose to a patient. Because of the (relatively) short half-lives of these types of radionuclides, a delay in patient administration may require a dynamic adjustment of the volume of the radionuclide solution. Even a delay of 15 minutes (for example, because of traffic delaying a patient's arrival at the test site) for the injection may significantly change the amount of solution volume necessary to supply a correct radionuclide dose. As such, the amount of radionuclide that is distributed to a treatment location typically exceeds the required dose. As a result, a technician is required to measure the activity level of the radionuclide and discard the excess radionuclide. This process is subject to errors in measurement by the technician and exposure of the technician to radiation from the disposal of the excess radionuclide. It is therefore useful to develop an injection syringe capable of on-the-fly adjustment of dose volume of a solution of a radionuclide material that reduces the risk of exposure to harmful radiation.

SUMMARY

The invention described in this document is not limited to the particular systems, methodologies or protocols described, as these may vary. The terminology used herein is for the purpose of describing particular embodiments only, and is not intended to limit the scope of the present disclosure.

It must be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

In an embodiment, an adjustable volume syringe device may include a delivery syringe having a delivery syringe barrel configured to hold a first amount of a fluid, a delivery syringe fluid port at a distal end of the delivery syringe barrel configured to dispense the fluid to a patient, a reservoir syringe having a reservoir syringe barrel configured to hold a second amount of the fluid, a reservoir syringe fluid port at a distal end of the reservoir syringe barrel configured to dispense the fluid into the delivery syringe barrel, and a reservoir plunger having a reservoir plunger body configured to cause one or more of at least a portion of the first amount of the fluid to be dispensed to a patient through the delivery syringe fluid port and at least a portion of the second amount of the fluid to be dispensed into the delivery syringe barrel through the reservoir syringe fluid port, and a reservoir plunger thumbpiece at a proximal end of the reservoir plunger. The reservoir syringe barrel is positioned at least partially within the delivery syringe barrel, and the reservoir plunger body is positioned at least partially within the reservoir syringe.

In an embodiment, a method of using an adjustable volume syringe having a delivery syringe, a reservoir syringe located at least in part within the delivery syringe, and a reservoir plunger located at least in part within the reservoir syringe may include storing a first amount of a fluid in the delivery syringe and a second amount of a fluid in the reservoir syringe, determining an administration amount of the fluid to administer to a patient, determining whether the administration amount is greater than the first amount, dispensing at least a portion of the second amount of the fluid from the reservoir syringe into the delivery syringe in response to the administration amount being greater than the first amount, and dispensing the administration amount of the fluid to the patient.

In an embodiment, a system for providing a fluid may include an adjustable volume syringe having a delivery syringe configured to contain a first amount of a fluid, a reservoir syringe configured to contain a second amount of the fluid and located at least in part within the delivery syringe, and a reservoir plunger located at least in part within the reservoir syringe, a dispensing module in mechanical communication with the adjustable volume syringe, a processor in operable communication with the dispensing module, and a non-transitory, computer-readable storage medium in operable communication with the processor. The computer-readable storage medium contains one or more programming instructions that, when executed, cause the processor to determine an administration amount of the fluid to administer, determine whether the administration amount is greater than the first amount, transmit one or more signals to cause the dispensing module to dispense at least a portion of the second amount of the fluid from the reservoir syringe into the delivery syringe in response to the administration amount being greater than the first amount, and transmit one or more signals to cause the dispensing module to dispense the administration amount of the fluid from the delivery syringe.

BRIEF DESCRIPTION OF THE DRAWINGS

FIGS. 3A and 3B depict cross-sectional views of an illustrative adjustable volume syringe before and after dispensing a fluid from a reservoir syringe to a delivery syringe according to an embodiment.

FIGS. 3C and 3D depict end views of an illustrative adjustable volume syringe before and after dispensing a fluid from a reservoir syringe by rotating a reservoir plunger according to an embodiment.

DETAILED DESCRIPTION

Figure 1A:
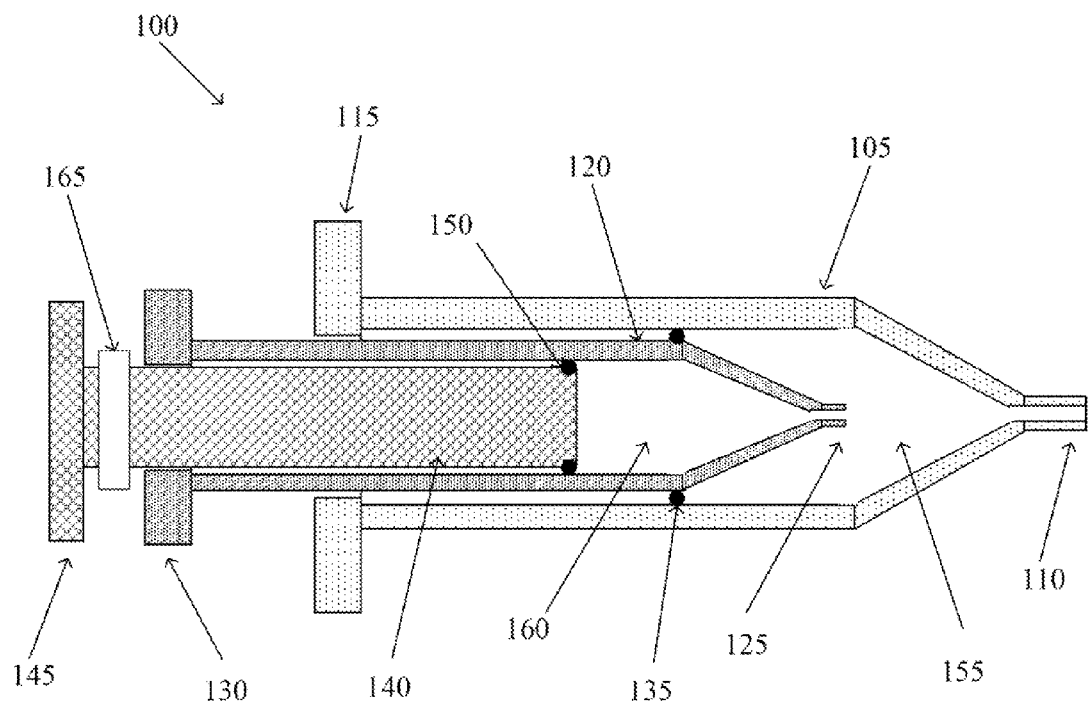
FIG. 1A depicts a cross-sectional view of an illustrative adjustable volume syringe according to an embodiment.

FIG. 1A depicts a cross-sectional view of an illustrative adjustable volume syringe according to an embodiment. As shown in FIG. 1A, the adjustable volume syringe 100 may substantially be a syringe-within-a-syringe. The delivery (outer) syringe may include a delivery syringe barrel 105, a delivery syringe fluid port 110 and a delivery syringe finger guard 115. A reservoir syringe may similarly include a reservoir syringe barrel 120, a reservoir syringe fluid port 125, and a reservoir syringe barrel end 130. The delivery syringe barrel 105 may be configured to hold a first amount of a fluid, such as a radionuclide, in a delivery space 155 formed between an exterior surface of the distal end of the reservoir syringe and the interior surface of the distal end of the delivery syringe. The reservoir syringe may act as a fluid plunger for the delivery syringe so that fluid within a delivery space 155 may be extruded or dispensed from the delivery syringe fluid port 110 as the reservoir syringe barrel end 130 is pressed towards the delivery syringe finger guard 115. In order to maintain pressure within the delivery space 155, the exterior surface of the reservoir syringe may include at least one reservoir syringe seal 135 configured to seal against the interior surface of the delivery syringe barrel 105. As such, the at least one reservoir syringe seal 135 may be positioned between the exterior surface of the reservoir syringe barrel 120 and the interior surface of the delivery syringe barrel 105. The at least one reservoir syringe seal 135 may comprise an O-ring or similar type of movable seal.

A reservoir plunger may be disposed at least partially within the reservoir syringe. The reservoir plunger may include a reservoir plunger body 140 and reservoir plunger thumb-piece 145. The position of the reservoir plunger may be adjusted with respect to the reservoir syringe barrel 120 by adjusting the position of the reservoir plunger thumb-piece 145 with respect to reservoir syringe barrel end 130. As the position of the reservoir plunger thumb-piece 145 is adjusted with respect to the reservoir plunger barrel end 130, the volume of the fluid within a reservoir space 160 that is formed between the exterior surface of the distal end of the reservoir plunger body 140 and the interior surface of the distal end of the reservoir syringe may be adjusted. If the reservoir plunger thumb-piece 145 is pushed towards the reservoir plunger barrel end 130, the fluid within the delivery space 160 may be extruded or dispensed from the reservoir syringe fluid port 125 into the delivery space 155 of the delivery syringe. In order to maintain pressure within the reservoir space 160, the exterior surface of the reservoir plunger body 140 may include at least one reservoir plunger seal 150 configured to seal against the interior surface of the reservoir syringe barrel 120. As such, the at least one reservoir plunger seal 150 may be positioned between the exterior surface of the reservoir plunger body 140 and the interior surface of the reservoir syringe barrel 120. The at least one reservoir plunger seal 150 may comprise an O-ring or similar type of movable seal.

Figure 1B:
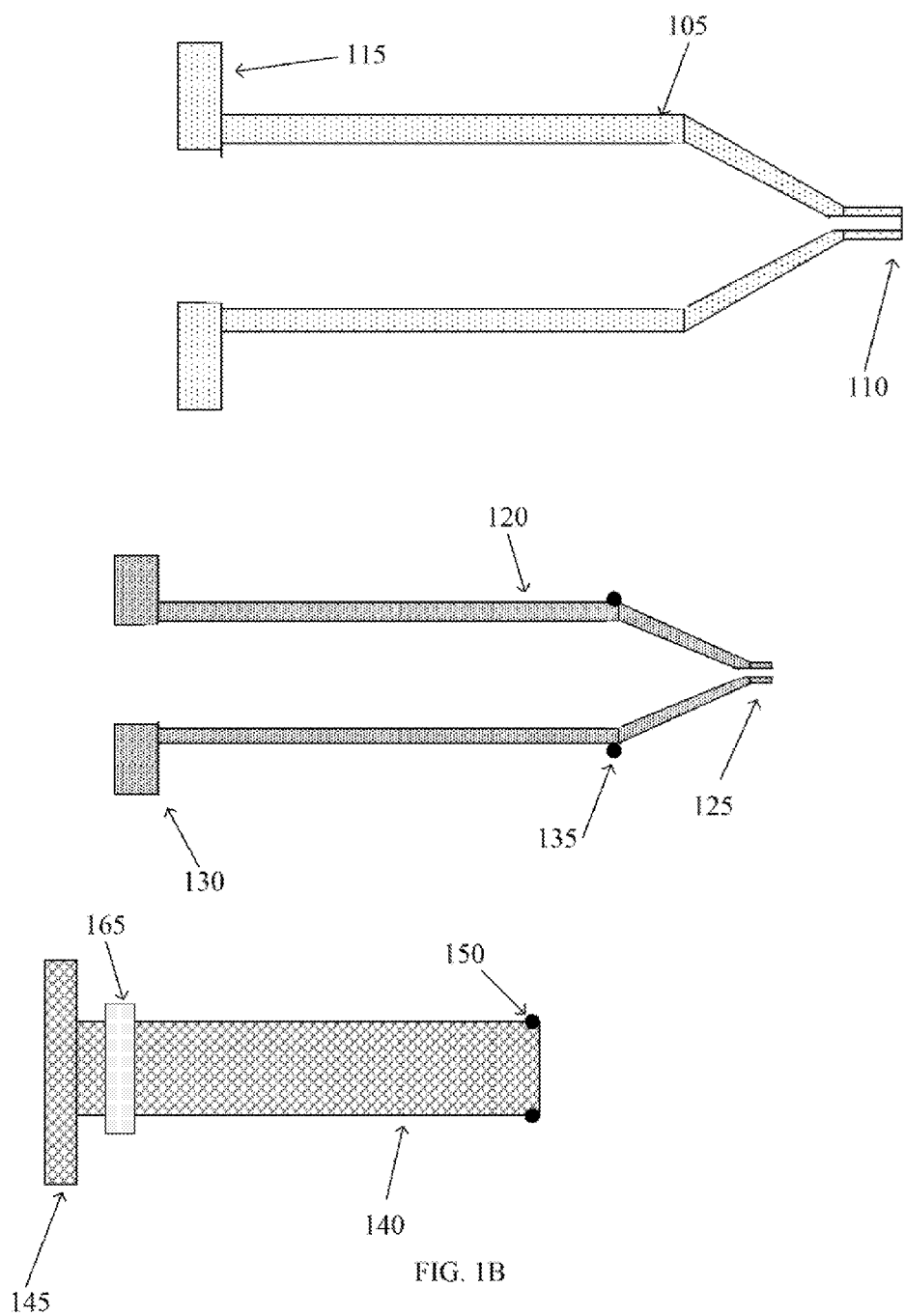
FIG. 1B depicts an exploded view of illustrative components of the adjustable volume syringe of FIG. 1A.

FIG. 1B depicts an exploded view of illustrative components of the adjustable volume syringe of FIG. 1A. The exploded view of FIG. 1B includes the delivery syringe comprising delivery the syringe barrel 105, the delivery syringe fluid port 110, and the delivery syringe finger guard 115. The exploded view further includes the reservoir syringe comprising the reservoir syringe barrel 120, the reservoir syringe fluid port 125, the reservoir syringe barrel end 130, and the at least one reservoir syringe seal 135. The exploded view additionally includes the reservoir plunger comprising the reservoir plunger body 140, reservoir plunger thumb-piece 145, and the at least one reservoir plunger seal 150.

In an embodiment, at least a portion of an exterior surface of the reservoir plunger body 140 may be threaded, and a threaded stop collar 165 may be located adjacent to the threaded portion of the reservoir plunger body. In an embodiment, the threaded reservoir plunger body 140 may include a scale which identifies an amount of fluid to dispense from the reservoir syringe barrel 120. The scale may be used to position the threaded stop collar 165 in order to dispense a proper amount of fluid from the delivery space 160 of the reservoir syringe. In such an embodiment, the threaded stop collar 165 may be positioned outside of the reservoir syringe barrel 120. When the reservoir syringe thumb-piece 145 is pushed, the threaded stop collar 165 may move with the reservoir plunger body 140 until it abuts the reservoir syringe barrel end 130. When the threaded stop collar 165 abuts the reservoir syringe barrel end 130, a proper amount of fluid may have been dispensed from the delivery space 160 of the reservoir syringe. The reservoir plunger body 140 and the reservoir syringe barrel 120 may then move in concert to dispense fluid in the delivery space 155 to a recipient.

In an embodiment, the reservoir syringe of FIGS. 1A and 1B may be used to remove fluid from the delivery syringe. In such an embodiment, a radionuclide, such as FDG, may be contained within the delivery space 155 of the delivery syringe. An amount of the radionuclide may be withdrawn from the delivery space 155 of the delivery syringe into the delivery space 160 of the reservoir syringe by pulling the reservoir plunger thumb-piece 145 in a proximal direction. When an appropriate amount of radionuclide has been withdrawn from the delivery space 155 of the delivery syringe, the reservoir plunger body 140 may be fixed with respect to the reservoir syringe barrel 120, and the radionuclide in the delivery space of the delivery syringe may be dispensed to a recipient through the delivery syringe fluid port 110 by moving the reservoir syringe body distally.

Figure 2A:
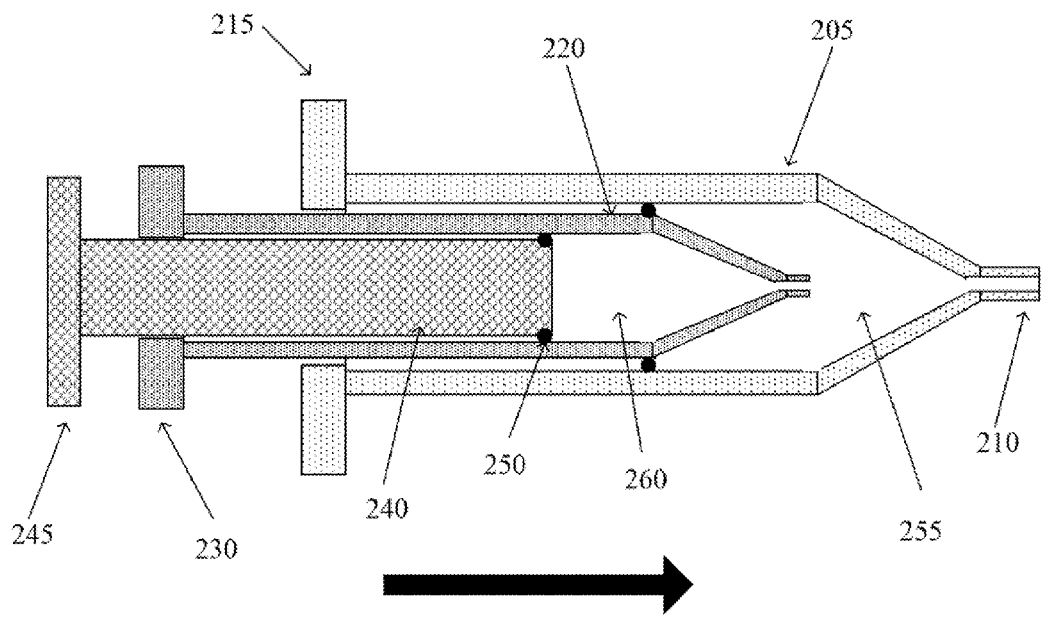
FIGS. 2A and 2B depict cross-sectional views of an illustrative adjustable volume syringe before and after dispensing a fluid from a delivery syringe according to an embodiment.
Figure 2B:
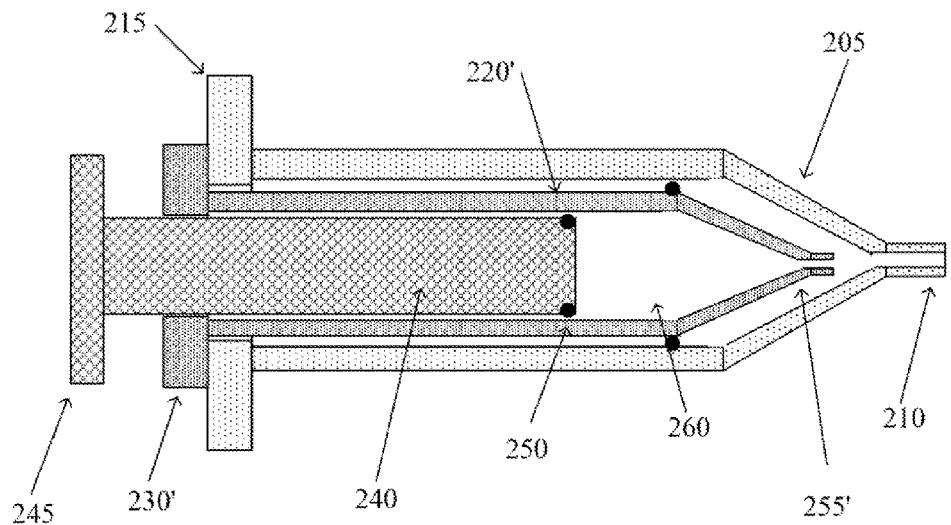

FIGS. 2A and 2B depict cross-sectional views of an illustrative adjustable volume syringe before and after dispensing a fluid from a delivery syringe according to an embodiment. More particularly, FIG. 2A illustrates an adjustable volume syringe when configured for injection, and FIG. 2B illustrates the adjustable volume syringe after an injection has been made. In an embodiment, an injection may be performed by pushing the reservoir syringe barrel end 230 from a pre-injection position (as illustrated in FIG. 2A) until it is disposed against the delivery syringe finger guard 215 at a post-injection position (230' in FIG. 2B), in the direction indicated by the arrow in FIG. 2A. In an embodiment, the friction of the at least one reservoir plunger seal 250 against the interior of the reservoir syringe barrel 220 may result in effectively no relative motion of the reservoir plunger 240 with respect to the reservoir syringe 220/220'. In an alternate embodiment, a key-lock mechanism (not shown) may permit a user to lock the reservoir plunger 240 with respect to the reservoir syringe 220/220' such that pushing on the reservoir plunger thumb-piece 245 will not result in movement of the reservoir plunger. Because the reservoir plunger 240 may be prevented from moving with respect to the reservoir syringe 220/220', the amount of fluid within the reservoir space 260 may remain substantially constant before (FIG. 2A) and after (FIG. 2B) the injection.

Prior to the injection (FIG. 2A), the distal end of the reservoir syringe may be disposed away from the distal end of the delivery syringe, thereby creating a delivery space 255. As the injection proceeds (FIG. 2B), the distal end of the reservoir syringe may approach the distal end of the delivery syringe, thereby reducing the volume of the delivery space 255'. The fluid from the delivery space 255 may then be extruded from the delivery syringe 205 through fluid port 210.

FIGS. 3A and 3B depict cross-sectional views of an illustrative adjustable volume syringe before and after dispensing a fluid from a reservoir syringe to a delivery syringe according to an embodiment. More particularly, FIG. 3A illustrates the adjustable volume syringe when configured for injection, and FIG. 3B illustrates a change in deliverable fluid volume based on a change in configuration of the adjustable volume syringe. In an embodiment, the reservoir plunger body 340 may be configured to move distally or proximally within the reservoir syringe barrel 320 when the reservoir syringe thumb-piece 345 is linearly displaced, as described in further detail below.

FIG. 3A illustrates an adjustable volume syringe preloaded with a volume of fluid in the delivery space 355 and an excess volume of fluid in the reservoir space 360. The reservoir plunger body 340 may be disposed at a location within the reservoir syringe barrel 320, and the reservoir syringe barrel may be disposed at a location within the delivery syringe barrel 305.

If the delivery volume is acceptable for a procedure, the fluid in the delivery space 355 may be injected through the delivery syringe fluid port 310 as illustrated in FIGS. 2A and 2B above. If the delivery volume is insufficient for the procedure, the deliverable fluid volume may be increased by withdrawing some fluid from the reservoir space 360 into the delivery space 355. Illustrative reasons for an insufficient delivery volume or amount of fluid may include a delay in performing the procedure.

Withdrawing the fluid from the reservoir space 360 into the delivery space 355 may be accomplished by occluding the delivery syringe fluid port 310, and moving the reservoir plunger thumb-piece 345 with respect to the reservoir syringe barrel end 330. FIG. 3A illustrates the relative motions of these two components by arrow A (relative direction of motion of the reservoir plunger thumb-piece 345) and arrow B (relative direction of motion of the reservoir syringe barrel end 330). Because the delivery syringe fluid port 310 is occluded, the sum of the fluid volume in the delivery space 355 and the fluid volume in the reservoir space 360 may be conserved. As such, a change from the initial position of the reservoir plunger thumb-piece 345 with respect to the reservoir syringe barrel end 330 results in a concomitant change in the position of the reservoir syringe barrel end with respect to the delivery syringe finger guard 315.

FIG. 3B illustrates the result of such fluid redistribution. The distance between the reservoir plunger thumb-piece 345' and the reservoir syringe barrel end 330' is decreased, thereby reducing the volume of the reservoir space 360'. The fluid previously held in the reservoir space 360 (FIG. 3A) may be injected into the delivery space 355', thereby increasing the volume of the delivery space. As a result of the increased volume in the delivery space 355', the reservoir syringe barrel 320' may adjust with respect to the delivery syringe barrel 305 and the distance between reservoir syringe barrel end 330' and the delivery syringe finger guard 315 increases from their initial positions.

FIGS. 3C and 3D depict end views of an illustrative adjustable volume syringe before and after dispensing a fluid from a reservoir syringe by rotating a reservoir plunger according to an embodiment. As shown in FIGS. 3A and 3B, the reservoir syringe body 320 and/or reservoir plunger 340 of an adjustable volume syringe may be moved with respect to the delivery syringe 305 in order to increase the amount of fluid stored in a delivery space 355 for injection to a patient. In an embodiment, linear displacements of the reservoir syringe body 320 and/or reservoir plunger 340 may be performed to increase the amount of fluid available for delivery to a patient. In an alternate embodiment, at least a portion of the reservoir plunger 340 and at least a portion of the reservoir syringe body 320 may be threaded. In such an embodiment, rotating the reservoir plunger 340 may cause the reservoir plunger to be displaced within the reservoir syringe body 320.

FIG. 3C illustrates an end view of the adjustable volume syringe of FIG. 3A prior to a fluid volume of the delivery space 355 being increased using a screw-actuated embodiment. In such an embodiment, the reservoir plunger thumb-piece 345 may be concentric with the reservoir syringe barrel end 330, and both are similarly concentric with the delivery syringe finger guard 315. In an embodiment, the delivery syringe finger guard 315 may include indicia 317 around its circumference. The indicia 317 may include any sort of marker including, but not limited to, lines, numbers, letters, and symbols. The reservoir plunger thumb-piece 345 may also have an indicator 347 that indicates a relative rotational position of the reservoir plunger thumb-piece 345 with respect to the reservoir syringe barrel end 330 or reservoir syringe body 320. FIG. 3C may represent an embodiment corresponding to the adjustable volume syringe configuration illustrated in FIG. 3A, prior to an adjustment to the volume in the delivery space 355.

FIG. 3D illustrates an end view of the adjustable volume syringe of FIG. 3B after a fluid volume of the delivery space 355' is increased using a screw-actuated embodiment. In such an embodiment, the indicator 347' may be directed towards a different indicium than the indicium towards which it was directed prior to the fluid volume of the delivery space 355' being increased. In other words, the reservoir plunger body 340' may be moved distally or proximally within the reservoir syringe body 320' in response to the reservoir plunger thumb-piece 345' being rotated.

In an embodiment, rotation of the reservoir plunger thumb-piece 345' may be accomplished manually by a user. In an alternate embodiment, rotation of the reservoir plunger thumb-piece 345' may be accomplished automatically through the use of, for example and without limitation, a transfer rod (not shown) and a controllable rotary motor (not shown). In yet another embodiment, automated rotation of the reservoir plunger thumb-piece 345' with respect to the reservoir syringe body 320' may be controlled by specific commands received from a user. In another embodiment, automated rotation of the reservoir plunger thumb-piece 345' with respect to the reservoir syringe body 320' may be performed based on an elapsed time from a time of initial syringe dose preparation.

Figure 4:
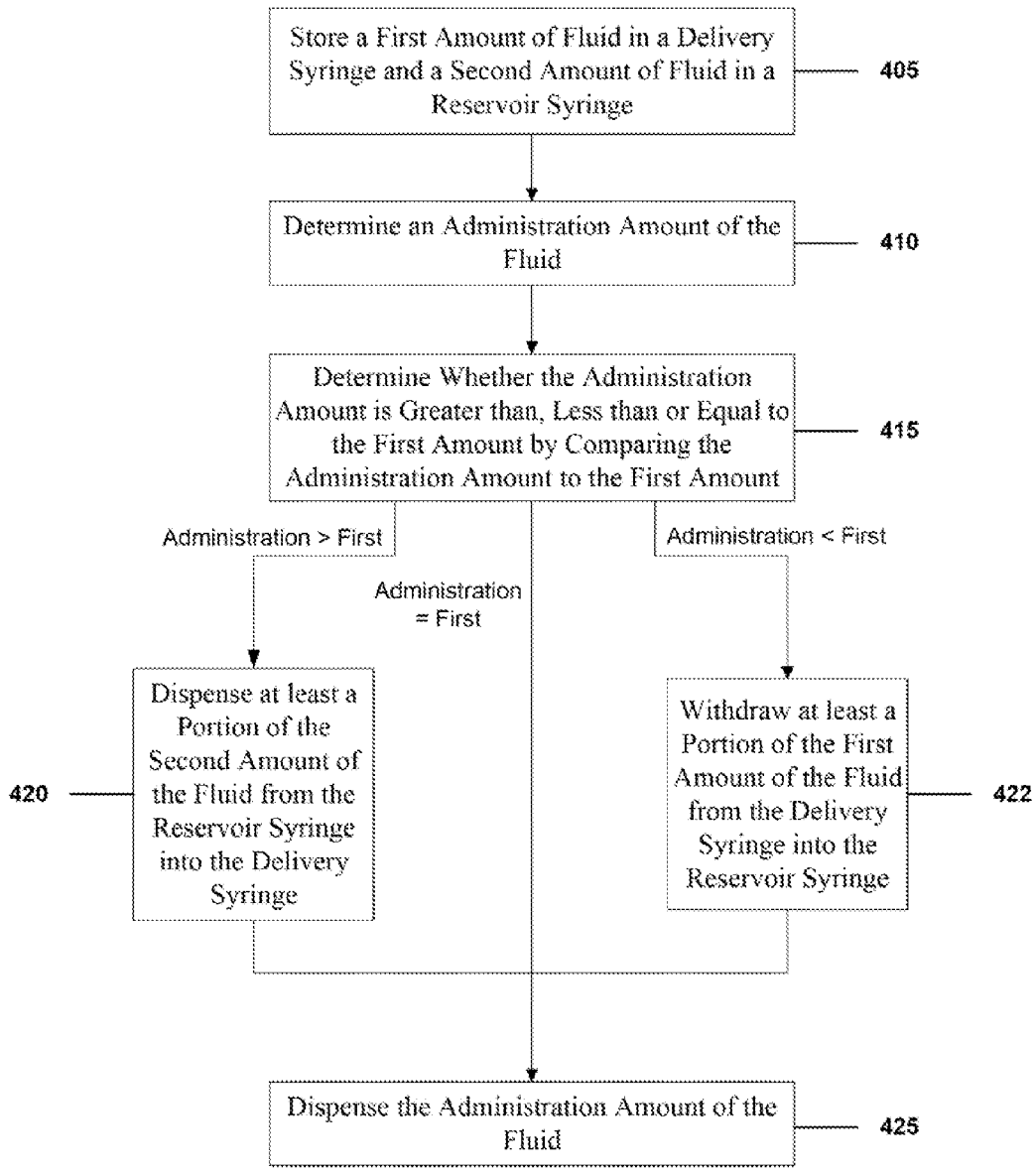
FIG. 4 depicts a flow diagram of an illustrative method of using an adjustable volume syringe according to an embodiment.

FIG. 4 depicts a flow diagram of an illustrative method of using an adjustable volume syringe according to an embodiment. The adjustable volume syringe has a delivery syringe, a reservoir syringe located at least in part within the delivery syringe, and a reservoir plunger located at least in part within the reservoir syringe. As shown in FIG. 4, first and second amounts of fluid may be stored 405 in the delivery syringe and the reservoir syringe, respectively. In an embodiment, the fluid may include a radionuclide. In an embodiment, the fluid may be one of $^{18}$F-deoxyglucose and $^{99m}$Tc or a $^{99m}$Tc containing compound or fluid. The first amount of fluid may correspond to a dosage to be delivered to a patient under an anticipated set of circumstances, such as a prescribed radioactivity dose at a particular time for a radionuclide. The second amount of fluid may correspond to an additional amount of the fluid.

An administration amount of the fluid may be determined 410. The administration amount of the fluid may be an amount to be administered to a recipient, such as a patient, as a part of a procedure. The administration amount may be determined 410 based on the type of fluid to be administered as well as one or more dosing requirements for the recipient. For example, if the fluid is a radionuclide, the administration amount may be determined 410 automatically, such as by a processing device, based on an expected administration time, an actual administration time and a required radioactivity to be dosed to the patient.

The administration amount may be compared with the first amount to determine 415 whether the administration amount is greater than, less than or equal to the first amount. The administration amount may be greater than the first amount if, for example, a delay occurred in the administration of a radionuclide. Because the radioactivity of radionuclides decays over time, if the actual administration time is later in time than the expected administration time, additional fluid may be required in order to achieve a required radioactivity. The administration amount may be less than the first amount if, for example, the entire amount of radionuclide is located in the delivery space of the delivery syringe and a portion of the first amount is to be withdrawn before administration to a patient.

At least a portion of the second amount of the fluid may be dispensed 420 from the reservoir syringe into the delivery syringe in response to the administration amount being greater than the first amount. The portion of the second amount of the fluid to be dispensed 420 into the delivery syringe may depend upon, for example, the amount of time that has elapsed since the anticipated administration time and the half-life of the fluid to be dispensed.

In an embodiment, at least a portion of an interior surface of the reservoir syringe and at least a portion of an exterior surface of the reservoir plunger may be threaded. In such an embodiment, dispensing 420 at least a portion of the second amount of the fluid may be performed by rotating the reservoir plunger within the reservoir syringe whereby the reservoir plunger moves distally into the reservoir syringe as a result of the threads. In an alternate embodiment, dispensing 420 at least a portion of the second amount of the fluid may be performed by pushing the reservoir plunger into the reservoir syringe such that the reservoir plunger moves distally into the reservoir syringe.

In an embodiment, the first amount of fluid can be automatically updated in real time to match the administration amount by dispensing 420 incremental amounts of the second amount of fluid from the reservoir syringe. For example, a controller, a processing device or the like could monitor an amount of time that has elapsed between an anticipated administration time and a current time and dispense 420 portions of the second amount of fluid into the delivery syringe over time so that the administration amount is present in the delivery syringe until the fluid is administered to the patient or the sum of the first amount of fluid and the second amount of fluid is less than the administration amount at a particular time.

At least a portion of the first amount of the fluid may be withdrawn 422 from the delivery syringe into the reservoir syringe in response to the administration amount being less than the first amount. The portion of the first amount of the fluid to be withdrawn 422 into the reservoir syringe may depend upon, for example, the amount of fluid that was originally stored in the delivery syringe, the administration time, and the half-life of the fluid to be dispensed.

In an embodiment, at least a portion of an interior surface of the reservoir syringe and at least a portion of an exterior surface of the reservoir plunger may be threaded. In such an embodiment, withdrawing 422 at least a portion of the first amount of the fluid may be performed by rotating the reservoir plunger within the reservoir syringe whereby the reservoir plunger moves proximally with respect to the reservoir syringe as a result of the threads. In an alternate embodiment, withdrawing 422 at least a portion of the first amount of the fluid may be performed by pulling the reservoir plunger from the reservoir syringe such that the reservoir plunger moves proximally with respect to the reservoir syringe.

The administration amount of the fluid may be dispensed 425 to the patient. In an embodiment, the administration amount of the fluid may be dispensed 425 by pushing the reservoir plunger. In an alternate embodiment, the administration amount of the fluid may be dispensed 425 by pushing a proximal end of the reservoir syringe.

Figure 5:
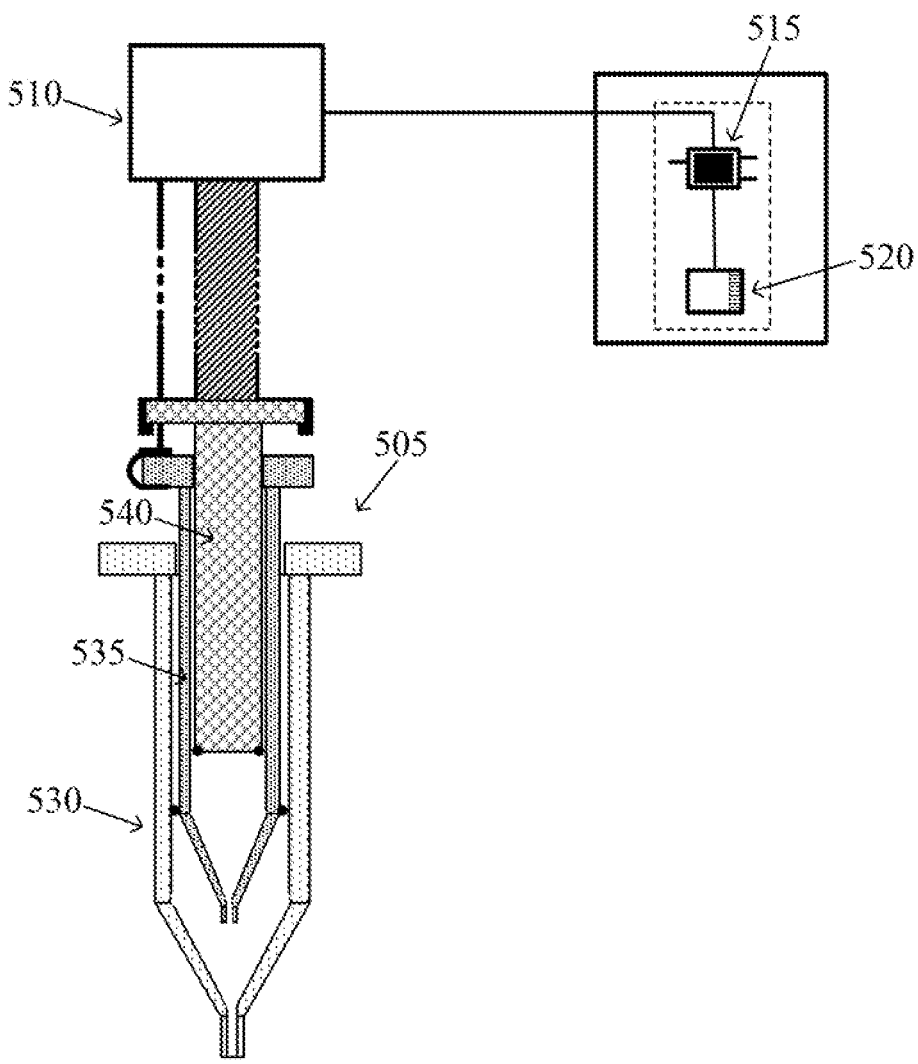
FIG. 5 depicts a block diagram of a system for providing a radionuclide to a patient according to an embodiment.

FIG. 5 depicts a partial block diagram of a system for providing a radionuclide to a patient according to an embodiment. As shown in FIG. 5, the system may include an adjustable volume syringe 505, a dispensing module 510, a processor 515 and a non-transitory, computer-readable storage medium 520.

The adjustable volume syringe 505 may be a syringe as described above in reference to any of FIGS. 1-4. The adjustable volume syringe 505 may include a delivery syringe 530, a reservoir syringe 535 located at least in part within the delivery syringe, and a reservoir plunger 540 located at least in part within the reservoir syringe. The delivery syringe 530 may be configured to contain a first amount of a fluid. The reservoir syringe 535 may be configured to contain a second amount of a fluid. In an embodiment, the fluid may be a radionuclide. In an embodiment, the fluid may include $^{18}$F-deoxyglucose. In an embodiment, the fluid may include $^{99m}$Tc.

The dispensing module 510 may be in mechanical communication with the adjustable volume syringe 505. For example, the dispensing module 510 may be in mechanical communication with the reservoir plunger 540 and/or a proximal end of the reservoir syringe 535. In an embodiment, the dispensing module 510 may comprise a motor drive that is used to move the reservoir plunger 540 and the proximal end of the reservoir syringe 535 independently.

The processor 515 may be in operable communication with the dispensing module 510. The computer-readable storage medium 520 may be in operable communication with the processor 515. The computer-readable storage medium 520 may contain one or more programming instructions that, when executed, cause the processor 515 to determine an administration amount of the fluid to administer, determine whether the administration amount is greater than the first amount, transmit one or more signals to cause the dispensing module 510 to dispense at least a portion of the second amount of the fluid from the reservoir syringe 535 into the delivery syringe 530 in response to the administration amount being greater than the first amount, and transmit one or more signals to cause the dispensing module to dispense the administration amount of the fluid from the delivery syringe.

In an embodiment, the one or more programming instructions that cause the processor 515 to determine an administration amount of the fluid may include one or more programming instructions that, when executed, cause the processor to determine an administration amount of the fluid based on an expected administration time, an actual administration time, and a required radioactivity.

In an embodiment, at least a portion of an interior surface of the reservoir syringe 535 and at least a portion of an exterior surface of the reservoir plunger 540 may be threaded. In such an embodiment, the one or more programming instructions that cause the processor 515 to transmit one or more signals that cause the dispensing module 510 to dispense at least a portion of the second amount of the fluid may include one or more programming instructions that, when executed, cause the processor to transmit one or more signals that cause the dispensing module to rotate the reservoir plunger 540 within the reservoir syringe 535. In such an embodiment, rotating the reservoir plunger 540 may cause the reservoir plunger to move distally into the reservoir syringe 535 as a result of the threads.

In an alternate embodiment, the one or more programming instructions that cause the processor 515 to transmit one or more signals that cause the dispensing module 510 to dispense at least a portion of the second amount of the fluid may include one or more programming instructions that, when executed, cause the processor to transmit one or more signals that cause the dispensing module to push the reservoir plunger 540 into the reservoir syringe 535. In such an embodiment, rotating the reservoir plunger 540 may cause the reservoir plunger to move distally into the reservoir syringe 535.

In an embodiment, the one or more programming instructions that cause the processor 515 to transmit one or more signals that cause the dispensing module 510 to dispense the administration amount of the fluid may include one or more programming instructions that, when executed, cause the processor to transmit one or more signals that cause the dispensing module to push the reservoir plunger 540. In an alternate embodiment, the one or more programming instructions that cause the processor 515 to transmit one or more signals that cause the dispensing module 510 to dispense the administration amount of the fluid may include one or more programming instructions that, when executed, cause the processor to transmit one or more signals that cause the dispensing module to push a proximal end of the reservoir syringe 535.

In an embodiment, the adjustable volume syringe 505 may be placed within a dose calibration chamber (not shown). The dose calibration chamber may be used to determine a radioactivity of a radionuclide stored within the adjustable volume syringe 505 at one or more particular times or in real time. The determined radioactivity of the radionuclide in the adjustable volume syringe may be communicated to the processor 515 which uses the information to determine whether to adjust the amount of radionuclide within the delivery syringe of the adjustable volume syringe 505. If the amount of radionuclide is to be adjusted, the processor 515 may direct the dispensing module 510 to adjust the amount of radionuclide by moving one or more of the reservoir plunger 540 and the proximal end of the reservoir syringe 535.

Figure 6:
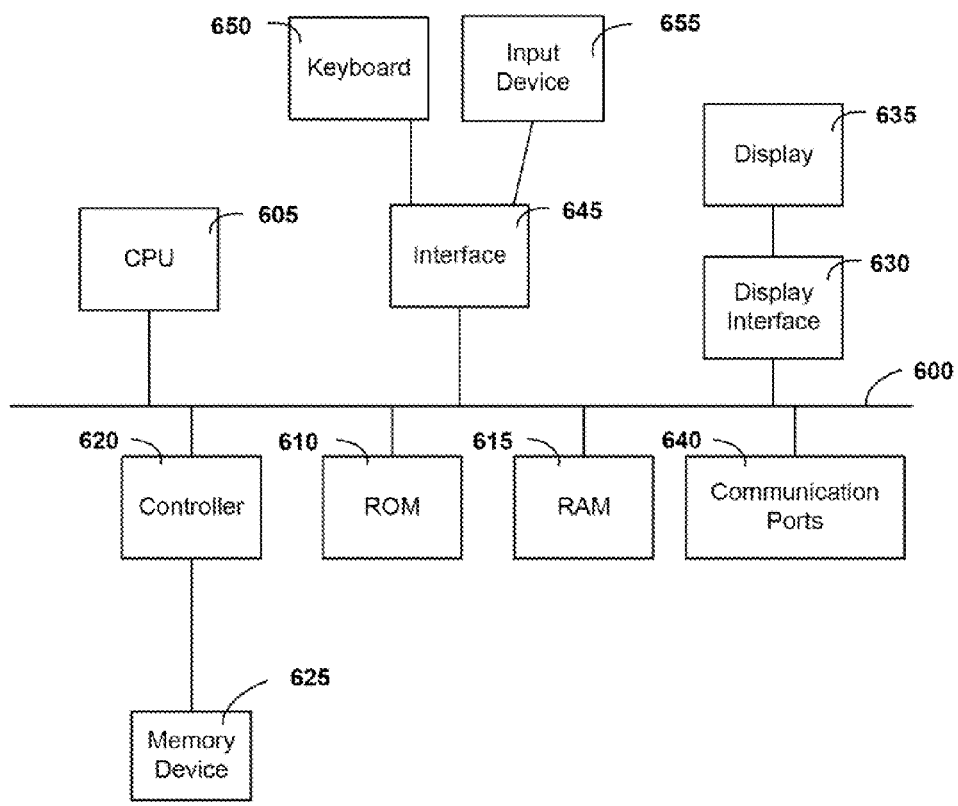
FIG. 6 depicts a block diagram of illustrative internal hardware that may be used to contain or implement program instructions according to an embodiment.

FIG. 6 depicts a block diagram of illustrative internal hardware that may be used to contain or implement program instructions, such as the process steps discussed above in reference to FIGS. 4 and/or 5, according to an embodiment. A bus 600 serves as the main information highway interconnecting the other illustrated components of the hardware. CPU 605 is the central processing unit of the system, performing calculations and logic operations required to execute a program. CPU 605, alone or in conjunction with one or more of the other elements disclosed in FIG. 5, is an illustrative processing device, computing device or processor as such terms are used within this disclosure. Read only memory (ROM) 610 and random access memory (RAM) 615 constitute illustrative memory devices (i.e., processor-readable non-transitory storage media).

A controller 620 interfaces with one or more optional memory devices 625 to the system bus 600. These memory devices 625 may include, for example, an external or internal DVD drive, a CD ROM drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 610 and/or the RAM 615. Optionally, the program instructions may be stored on a tangible computer readable medium such as a compact disk, a digital disk, flash memory, a memory card, a USB drive, an optical disc storage medium, such as a Blu-ray™ disc, and/or other non-transitory storage media.

An optional display interface 630 may permit information from the bus 600 to be displayed on the display 635 in audio, visual, graphic or alphanumeric format. Communication with external devices, such as a print device, may occur using various communication ports 640. An illustrative communication port 640 may be attached to a communications network, such as the Internet or an intranet.

The hardware may also include an interface 645 which allows for receipt of data from input devices such as a keyboard 650 or other input device 655 such as a mouse, a joystick, a touch screen, a remote control, a pointing device, a video input device and/or an audio input device. In an embodiment, the interface 645 may receive data from a dose calibration chamber or other activity detector.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A system for providing a fluid, the system comprising:
an adjustable volume syringe having a delivery syringe barrel, a reservoir syringe barrel positioned at least partially within and in fluid communication with the delivery syringe barrel, and a reservoir plunger positioned at least partially within the reservoir syringe barrel, wherein the delivery syringe barrel is configured to contain a first amount of a fluid, wherein the reservoir syringe barrel is configured to contain a second amount of the fluid;
a dispensing module in mechanical communication with the adjustable volume syringe;
a processor in operable communication with the dispensing module; and
a non-transitory, computer-readable storage medium in operable communication with the processor,
wherein the non-transitory, computer-readable storage medium contains one or more programming instructions that, when executed, cause the processor to:
determine an administration amount of the fluid to administer;
determine whether the administration amount is greater than, less than, or equal to the first amount of the fluid;
transmit one or more signals to cause the dispensing module to adjust the first amount of the fluid in the delivery syringe barrel to equal the administration amount by increasing or decreasing the second amount of the fluid in the reservoir syringe barrel, and
transmit one or more signals to cause the dispensing module to dispense the administration amount of the fluid from the delivery syringe barrel by moving the reservoir syringe barrel with respect to the delivery syringe barrel to deliver the first amount of the fluid.

2. The system of claim 1, wherein the fluid comprises a radionuclide.

3. The system of claim 2, wherein the one or more programming instructions that cause the processor to determine an administration amount of the fluid comprise one or more programming instructions that, when executed, cause the processor to determine the administration amount of the fluid based on an expected administration time, an actual administration time, and a required radioactivity.

4. The system of claim 1, wherein at least a portion of an interior surface of the reservoir syringe barrel and at least a portion of an exterior surface of the reservoir plunger are threaded.

5. The system of claim 4, wherein the one or more programming instructions that cause the processor to transmit one or more signals to cause the dispensing module to adjust the first amount of the fluid in the delivery syringe barrel to equal the administration amount comprise one or more programming instructions that, when executed, cause the processor to transmit one or more signals to cause the dispensing module to rotate the reservoir plunger to adjust the second amount of the fluid.

6. The system of claim 1, wherein the one or more programming instructions that cause the processor to transmit one or more signals to cause the dispensing module to increase or decrease the second amount of the fluid comprise one or more programming instructions that, when executed, cause the processor to transmit one or more signals to cause the dispensing module to move the reservoir plunger with respect to the reservoir syringe barrel.

7. The system of claim 1, wherein:
the delivery syringe barrel has a proximal end and a distal end, and a delivery syringe fluid port at the distal end of the delivery syringe barrel;
the reservoir syringe barrel has a proximal end and a distal end, and a reservoir syringe fluid port at the distal end of the reservoir syringe barrel; and
the reservoir plunger comprises a reservoir plunger body;
wherein the adjustable volume syringe further comprises a delivery space formed between an exterior surface of the reservoir syringe barrel and an interior surface of the delivery syringe barrel, the delivery space configured to hold the first amount of the fluid; and
a reservoir space formed between an exterior surface of the reservoir plunger body and an interior surface of the reservoir syringe barrel, the reservoir space configured to hold the second amount of the fluid,
wherein the reservoir plunger is movable in a first direction to dispense at least a portion of the second amount of the fluid from the reservoir space into the delivery space to increase an administration amount of the fluid, and
wherein the reservoir plunger is movable in a second direction to withdraw at least a portion of the first amount of the fluid from the delivery space into the reservoir space to decrease the administration amount of the fluid.

8. The system of claim 7, wherein the adjustable volume syringe further comprises:
a reservoir syringe seal positioned between the exterior surface of the reservoir syringe barrel and the interior surface of the delivery syringe barrel.

9. The system of claim 8, wherein the reservoir syringe seal comprises an O-ring.

10. The system of claim 7, wherein the adjustable volume syringe further comprises:
at least one reservoir plunger seal positioned between the exterior surface of the reservoir plunger body and the interior surface of the reservoir syringe barrel.

11. The system of claim 10, wherein the at least one reservoir plunger seal comprises an O-ring.

12. The system of claim 7, wherein the reservoir plunger further comprises:
a reservoir plunger thumb-piece at a proximal end of the reservoir plunger, wherein the reservoir plunger body is configured to move distally or proximally within the reservoir syringe barrel when the reservoir plunger thumb-piece is linearly displaced.

13. The system of claim 7, wherein at least a portion of the interior surface of the reservoir syringe barrel and at least a portion of the exterior surface of the reservoir plunger body are threaded.

14. The system of claim 13, wherein the reservoir plunger further comprises: a reservoir plunger thumb-piece at a proximal end of the reservoir plunger, wherein the reservoir plunger body is configured to move distally or proximally within the reservoir syringe barrel when the reservoir plunger thumb-piece is rotated.

\* \* \* \* \*